US010426739B2

(12) United States Patent
Knutson

(10) Patent No.: US 10,426,739 B2
(45) Date of Patent: Oct. 1, 2019

(54) ADHESIVE PATCH ASSEMBLY WITH OVERLAY LINER AND SYSTEM AND METHOD FOR MAKING SAME

(71) Applicant: 3M INNOVATIVE PROPERTIES COMPANY, St. Paul, MN (US)

(72) Inventor: Gordon P. Knutson, Beldenville, WI (US)

(73) Assignee: 3M Innovative Properties Company, Saint Paul, MN (US)

( * ) Notice: Subject to any disclaimer, the term of this patent is extended or adjusted under 35 U.S.C. 154(b) by 11 days.

(21) Appl. No.: 14/352,328

(22) PCT Filed: Dec. 12, 2012

(86) PCT No.: PCT/US2012/069037
§ 371 (c)(1),
(2) Date: Apr. 17, 2014

(87) PCT Pub. No.: WO2013/096027
PCT Pub. Date: Jun. 27, 2013

(65) Prior Publication Data
US 2014/0303574 A1 Oct. 9, 2014

Related U.S. Application Data

(60) Provisional application No. 61/578,567, filed on Dec. 21, 2011.

(51) Int. Cl.
*A61F 13/00* (2006.01)
*A61K 9/70* (2006.01)
(Continued)

(52) U.S. Cl.
CPC ........ *A61K 9/7076* (2013.01); *A61F 13/0008* (2013.01); *A61F 13/0259* (2013.01);
(Continued)

(58) Field of Classification Search
CPC ...... A61K 9/70; A61K 31/485; A61K 9/7076; A61F 13/00072; A61F 13/00076; A61F 13/0008; A61F 13/00063; A61F 13/0259
(Continued)

(56) References Cited

U.S. PATENT DOCUMENTS 2,703,083 A * 3/1955 Gross ...................... A61F 13/02
156/248
2,946,435 A * 7/1960 Schladermundt ... A61F 13/0203
206/441

(Continued)

FOREIGN PATENT DOCUMENTS

DE 102006011338 9/2007
EP 2 065 021 6/2009
(Continued)

OTHER PUBLICATIONS

International Search Report for PCT Application No. PCT/US2012/069037 dated May 23, 2013, 3 pages.

*Primary Examiner* — Kim M Lewis
(74) *Attorney, Agent, or Firm* — 3M Innovative Properties Company; Ted K. Ringsred

(57) ABSTRACT

An adhesive patch assembly and method for making same. The assembly can include an adhesive patch and a release liner. The patch can include a backing and a skin-contact adhesive. The release liner can further include a first portion and a second portion separated by a hinge. The first portion can be positioned to overlay the backing of the patch when the release liner is folded upon the hinge, and the second portion can be positioned to underlie the skin-contact adhesive of the patch. The method can include positioning the patch on the release liner, such that patch is located on one of the first portion and the second portion of the release liner; and folding the release liner about to locate the patch
(Continued)

between the first portion and the second portion of the release liner.

21 Claims, 5 Drawing Sheets

(51) Int. Cl.
| | |
|---|---|
| A61F 13/02 | (2006.01) |
| A61K 31/167 | (2006.01) |
| A61K 31/196 | (2006.01) |
| A61K 31/34 | (2006.01) |
| A61K 31/4168 | (2006.01) |
| A61K 31/439 | (2006.01) |
| A61K 31/4439 | (2006.01) |
| A61K 31/4458 | (2006.01) |
| A61K 31/485 | (2006.01) |
| A61K 31/565 | (2006.01) |
| A61K 31/567 | (2006.01) |
| B32B 37/26 | (2006.01) |
| C09J 7/40 | (2018.01) |

(52) U.S. Cl.
CPC .......... *A61K 9/703* (2013.01); *A61K 9/7084* (2013.01); *A61K 31/167* (2013.01); *A61K 31/196* (2013.01); *A61K 31/34* (2013.01); *A61K 31/4168* (2013.01); *A61K 31/439* (2013.01); *A61K 31/4439* (2013.01); *A61K 31/4458* (2013.01); *A61K 31/485* (2013.01); *A61K 31/565* (2013.01); *A61K 31/567* (2013.01); *B32B 37/26* (2013.01); *C09J 7/403* (2018.01); *A61F 2013/008* (2013.01); *A61F 2013/00646* (2013.01); *B32B 2037/268* (2013.01); *Y10T 156/1049* (2015.01); *Y10T 428/1476* (2015.01)

(58) Field of Classification Search
USPC .............. 602/41, 42, 57, 900; 206/441, 440
See application file for complete search history.

(56) References Cited

U.S. PATENT DOCUMENTS

| | | | | |
|---|---|---|---|---|
| 2,969,144 | A | * | 1/1961 | Zackheim .......... A61F 13/0203 206/441 |
| 3,018,881 | A | | 1/1962 | Wall |
| 3,256,881 | A | * | 6/1966 | Stenvall ............. A61F 13/0203 206/441 |
| 3,531,847 | A | * | 10/1970 | Wallerstein ........ A61F 13/0276 29/411 |
| 4,472,480 | A | | 9/1984 | Olson |
| 4,584,355 | A | | 4/1986 | Blizzard |
| 4,585,836 | A | | 4/1986 | Homan |
| 4,591,622 | A | | 5/1986 | Blizzard |
| 4,655,767 | A | | 4/1987 | Woodard |
| 4,693,776 | A | | 9/1987 | Krampe |
| 4,751,087 | A | | 6/1988 | Wick |
| 4,834,979 | A | | 5/1989 | Gale |
| 4,915,102 | A | | 4/1990 | Kwiatek |
| 5,223,261 | A | | 6/1993 | Nelson |
| 5,232,702 | A | * | 8/1993 | Pfister ................. A61K 9/7069 424/448 |
| 5,333,753 | A | * | 8/1994 | Etheredge ............ A61F 15/001 206/441 |
| 5,380,760 | A | | 1/1995 | Wendel |
| 5,531,855 | A | | 7/1996 | Heinecke |
| 5,656,286 | A | | 8/1997 | Miranda |
| 5,688,523 | A | | 11/1997 | Garbe |
| 5,783,269 | A | | 7/1998 | Heilmann |
| 5,916,587 | A | * | 6/1999 | Min ..................... A61K 9/7061 424/448 |
| 5,950,830 | A | | 9/1999 | Trigger |
| 6,004,578 | A | | 12/1999 | Lee |
| 6,024,976 | A | | 2/2000 | Miranda |
| 6,129,929 | A | | 10/2000 | Wick |
| 6,142,954 | A | | 11/2000 | Anhauser |
| 6,149,935 | A | | 11/2000 | Chiang |
| 6,365,178 | B1 | | 4/2002 | Venkateshwaran |
| 7,506,760 | B2 | | 3/2009 | Grossman |
| 2003/0054025 | A1 | | 3/2003 | Cantor |
| 2004/0049150 | A1 | | 3/2004 | Dalton |
| 2004/0202708 | A1 | | 10/2004 | Roehrig |
| 2006/0270959 | A1 | * | 11/2006 | Parker ................. A61F 13/0203 602/57 |
| 2007/0073211 | A1 | * | 3/2007 | Propp .................. A61M 25/02 602/57 |
| 2007/0173752 | A1 | * | 7/2007 | Schonfeldt ........... A61F 15/001 602/57 |
| 2008/0172015 | A1 | | 7/2008 | Okada et al. |
| 2008/0274146 | A1 | | 11/2008 | Bartholomaus |
| 2009/0216169 | A1 | * | 8/2009 | Hansen ................ A61F 15/001 602/48 |
| 2010/0056972 | A1 | | 3/2010 | Harima |
| 2010/0158991 | A1 | | 6/2010 | Okada |
| 2010/0292660 | A1 | | 11/2010 | Kydonieus |
| 2011/0288463 | A1 | * | 11/2011 | Girasa ................. A61F 15/002 602/57 |
| 2013/0012859 | A1 | * | 1/2013 | Krohn ............... A61F 13/00076 602/57 |
| 2014/0288478 | A1 | * | 9/2014 | Holubec ............. A61F 13/0259 602/57 |

FOREIGN PATENT DOCUMENTS

| | | |
|---|---|---|
| JP | 5-54515 | 7/1983 |
| JP | 61-203020 | 12/1986 |
| JP | 1-155428 | 10/1989 |
| JP | 02270818 A * | 11/1990 |
| JP | 2006-204633 | 8/2006 |
| JP | 2008-188414 | 8/2008 |
| JP | 2009-114139 | 5/2009 |
| JP | 2011-084338 A | 4/2011 |
| WO | WO 2007101660 | 9/2007 |
| WO | WO 2011-066493 | 6/2011 |

* cited by examiner

ADHESIVE PATCH ASSEMBLY WITH OVERLAY LINER AND SYSTEM AND METHOD FOR MAKING SAME

CROSS REFERENCE TO RELATED APPLICATIONS

This is a national stage filing under 35 U.S.C. § 371 of PCT Application No. PCT/US2012/069037, filed Dec. 12, 2012, which claims priority to U.S. Provisional Application No. 61/578,567, filed Dec. 21, 2011, the disclosure of which is incorporated herein by reference in its entirety.

FIELD

The present disclosure generally relates to adhesive patch assemblies comprising an adhesive patch and a release liner, and more particularly, to assemblies comprising a transdermal adhesive patch that can be used to deliver an active ingredient via skin.

BACKGROUND

Adhesive patches can be used for a variety of purposes, including wound protection and/or treatment, continuous transdermal administration of an active ingredient (e.g., a drug), or combinations thereof.

In general, an adhesive patch comprises a support or backing that can be made of a cloth, a plastic film, or the like, and an adhesive layer laminated on the backing. The adhesive patch is generally provided with a release liner laminated on the adhesive layer and packaged in a package (e.g., made of a resin film). In some adhesive patches, components of the adhesive layer can protrude from the edge of the adhesive patch, e.g., via cold flow, which can pose problems during manufacture, shipment, storage, and use. In addition or alternatively, sometimes handling of the patch can cause oozing of the adhesive.

Cold flow can occur depending on the property of an adhesive, and can occur as a result of the adhesive patch being under a load for a long time, for example, when an adhesive patch is contained in a package and stored for a period of time prior to use. Cold flow of the adhesive layer in adhesive patches can inhibit the removal of the adhesive patch from a package, which can be caused by adhesion of protruded adhesive layer components to the inside of the package.

SUMMARY

Transdermal drug-in-adhesive systems are typically loaded with skin penetration enhancers and drugs, sometimes in the form of an oily substance, which can contribute to a condition known as cold-flow, in which the adhesive at the edges of the die-cut patch can creep out from under the backing over time, and adhere the patch to a pouch or packaging material in which the assembly is packaged. To address this problem, some existing systems or assemblies include a second release liner that is placed over the adhesive patch with its release side oriented toward the patch in order to prevent cold flow from adhering the unstable adhesive to packaging material. However, such second release liners tend to move out of the desired position during manufacture, shipment and storage of the packaged adhesive patch assemblies. The adhesive patch assemblies of the present disclosure address the issues of adhesive creep and cold flow, as well as release liner movement. Some embodiments of the adhesive patch assemblies of the present disclosure can address the problem of adhesive patch assemblies adhering to the inside of packaging material (e.g., which can at least partially be a result of the drug-in-adhesive formulation that is used).

One aspect of the present disclosure provides an adhesive patch assembly. The assembly can include a patch and a release liner. The patch can include a backing having a first major surface and a second major surface opposite the first major surface, and a skin-contact adhesive coupled to the second major surface of the backing. The release liner can include a first major surface and a second major surface opposite the first major surface, at least the first major surface configured to present release characteristics relative to the skin-contact adhesive of the patch. The release liner can further include a first portion and a second portion separated by a hinge. The first portion can be positioned to overlay the first major surface of the backing of the patch when the release liner is folded upon the hinge, and the second portion can be positioned to underlie at least one of the second major surface of the backing and the skin-contact adhesive of the patch. The assembly can be configured such that the first major surface of the release liner is positioned to face the patch when the patch is located between the first portion and the second portion of the release liner.

Another aspect of the present disclosure also provides an adhesive patch assembly. The assembly can include all of the feature of the aspect above, and can be further configured such that the coefficient of adhesion between the first major surface of the release liner and the backing of the patch is less than the coefficient of adhesion between the first major surface of the release liner and the skin-contact adhesive of the patch.

Another aspect of the present disclosure provides a method of making an adhesive patch assembly. The method can include providing a patch and a providing a release liner. The patch can include a backing and a skin-contact adhesive coupled to the backing. The release liner can include a first portion and a second portion, and each of the first portion and the second portion can be dimensioned to accommodate the patch. The method can further include positioning the patch on the release liner, such that patch is located on the second portion of the release liner, and the first portion of the release liner is free of the patch. The method can further include folding the release liner about a hinge located between the first portion and the second portion to locate the patch between the first portion and the second portion of the release liner.

Other features and aspects of the present disclosure will become apparent by consideration of the detailed description and accompanying drawings.

DETAILED DESCRIPTION

Figure 1:
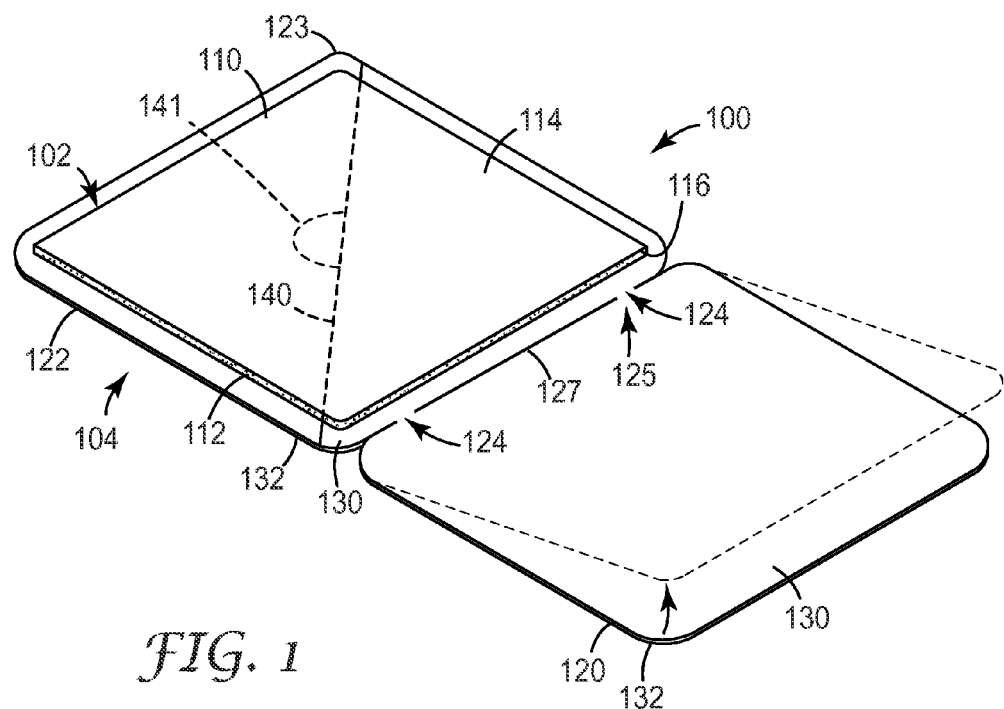
FIG. 1 is a perspective view of an adhesive patch assembly according to one embodiment of the present disclosure, the adhesive patch assembly shown unassembled.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the term "coupled," and variations thereof, is used broadly and encompasses both direct and indirect couplings. It is to be understood that other embodiments may be utilized, and structural or logical changes may be made without departing from the scope of the present disclosure. Furthermore, terms such as "first," "second," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to an adhesive patch assembly that includes an adhesive patch positioned between an overlaid release liner (or "cover liner" or "secondary release liner") and a primary release liner ("primary liner"), where the cover liner is at least partially attached to the primary liner, so as to prevent the cover liner from moving out of protective position during manufacture, shipment, or storage of the packaged adhesive patch assembly. In some embodiments, the primary liner and the cover liner can be at least partially coupled to one another and separated from one another by at least one of a fold and a hinge, such that the adhesive patch can be located between the two portions of the folded release liner during storage. As such, the adhesive patch assembly, and the release liner, of the present disclosure can be referred to as including an overlay liner, which in some embodiments, can include an integral overlay liner.

The present disclosure further provides methods of manufacturing an adhesive patch assembly in which the cover liner can be coupled to the primary liner (e.g., integrally formed therewith), and folded over the adhesive patch on the converting line. Some embodiments of the present disclosure include a secondary process and mechanism by which the adhesive patch and release liner (i.e., with the primary liner and the cover liner) is placed upon a lower packaging foil of a pouch-forming packaging line independently of packaging foil speed. Such a secondary process can be accomplished, for example, with the use of belted conveyors to remove the adhesive patch assembly from a liner die and place it on the packaging foil. Exemplary methods of the present disclosure are described in greater detail below with respect to FIGS. 6-7F.

Figure 2:
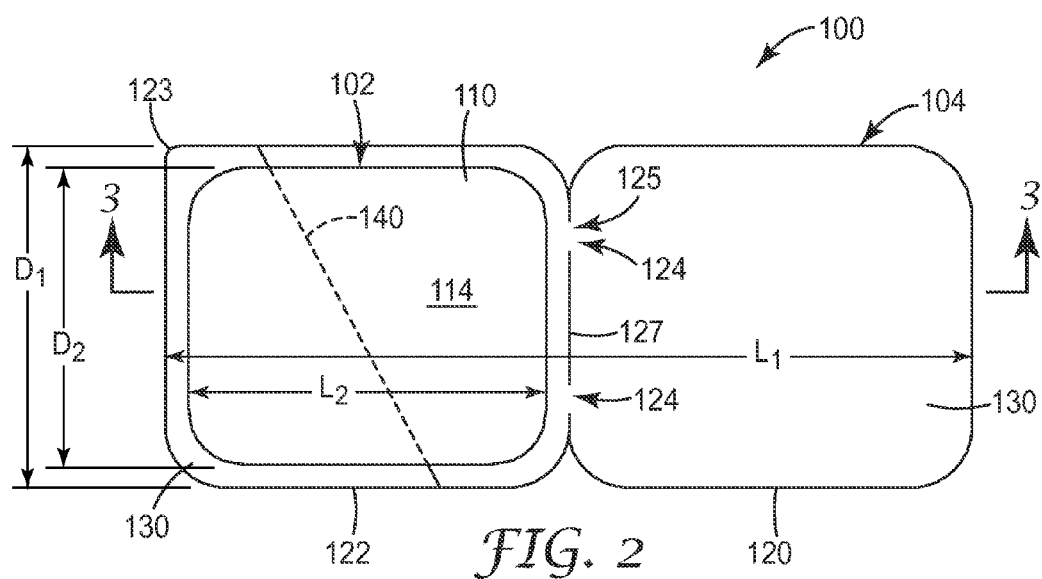
FIG. 2 is a top plan view of the adhesive patch assembly of FIG. 1.
Figure 3:
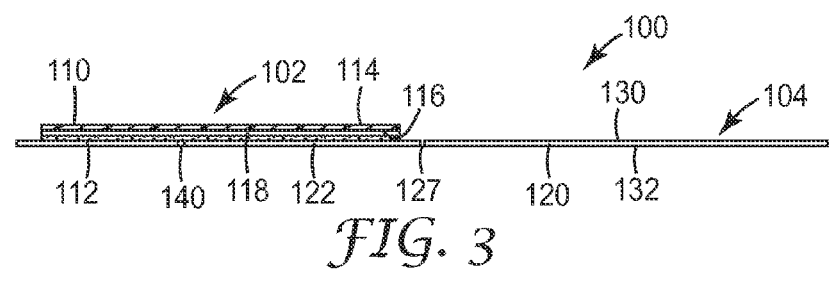
FIG. 3 is a schematic side cross-sectional view of the adhesive patch assembly of FIGS. 1 and 2, taken along line 3-3 of FIG. 2.
Figure 4:
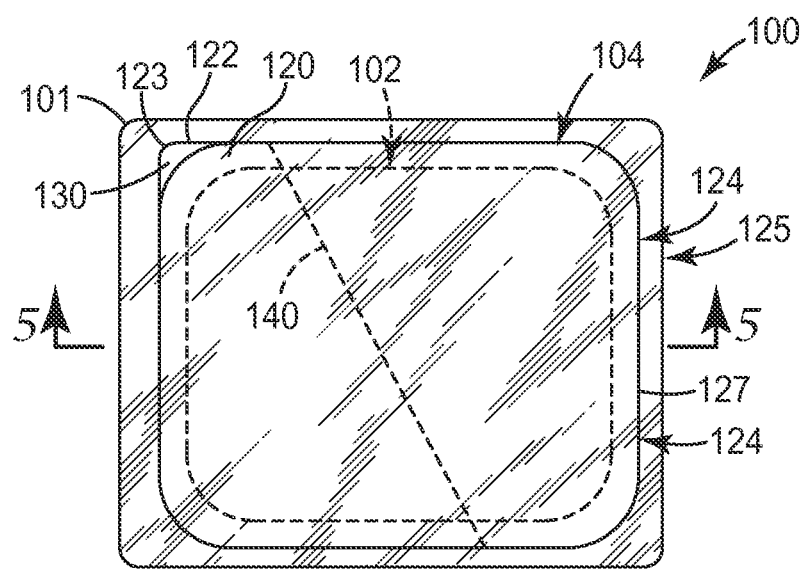
FIG. 4 is a top plan view of the adhesive patch assembly of FIGS. 1-3, the adhesive patch assembly shown assembled and enclosed in a pouch.
Figure 5:
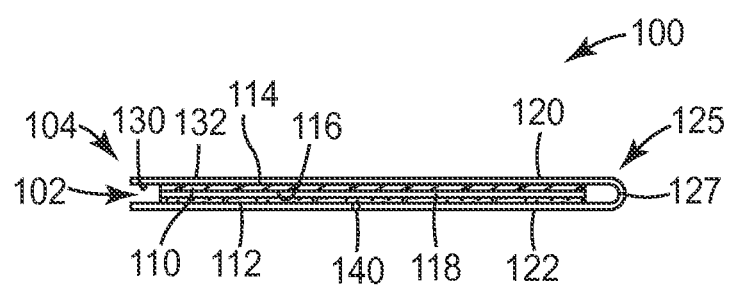
FIG. 5 is a schematic side cross-sectional view of the adhesive patch assembly of FIGS. 1-4, shown assembled, taken along line 5-5 of FIG. 4, with the pouch removed for clarity.

FIGS. 1-5 illustrate an adhesive patch assembly 100 according to one embodiment of the present disclosure. FIGS. 1-3 show the adhesive patch assembly 100 unassembled, i.e., in a first, or unfolded, configuration. FIGS. 4-5 show the adhesive patch assembly 100 assembled, i.e., in a second, or folded, configuration. As shown in FIG. 4, in some embodiments, the adhesive patch assembly 100 can be packaged in a pouch 101 or other packaging material, which can be hermetically sealed. By way of example only, the pouch 101 is shown as being transparent; however, this need not be the case. Such a pouch 101 or packaging material can be foil-lined and/or can be hermetically-sealed. Other materials, such as multi-laminate polymer films (e.g., with low moisture and/or oxygen permeability) may also be suitable for the pouch 101. Laminates may include layers of polyester; polyethylene; foil (e.g., aluminum foil); BAREX™ impact-modified acrylonitrile-methyl acrylate copolymers (available from INEOS, Lausanne, Switzerland); polyacrylonitrile copolymer; SURLYN™ thermoplastic ionomer resin (available from E.I. du Pont de Nemours and Company, Wilmington, Del.); paper; and deposited inorganic barrier layers, such as those described in U.S. Patent Application Publication No. 2004/0202708; or combinations thereof. One or more of these layers may be heat-sealable in order to facilitate pouch sealing. In order to improve storage stability, an optional desiccant and/or oxygen absorber may also be included within the pouch 101. Adhesive patch assemblies of the present disclosure may alternatively be provided in a rolled or stacked form suitable for use with a dispensing apparatus.

As shown in FIGS. 1-5, the adhesive patch assembly 100 can include an adhesive patch 102 and a release liner 104. In some embodiments, the adhesive patch 102 can include a transdermal drug delivery patch comprising a drug that can be administered via skin, particularly, mammalian skin, and particularly transdermally.

With continued reference to FIGS. 1-5, the patch 102 can include a backing 110, and an adhesive 112, e.g., a skin-contact adhesive (such adhesive can also be referred to as an "adhesive layer" or a "skin-contact layer"). The backing 110 can include a first major surface 114 and a second major surface 116 opposite the first major surface 114, and the skin-contact adhesive 112 can be coupled (i.e., directly, or indirectly via one or more optional additional layers, as described below) to the second major surface 116.

The release liner 104 can include a first portion 120 and a second portion 122 that are at least partially coupled to one another and separated by at least one of a fold and/or hinge 125, such that the first portion 120 and the second portion 122 can be folded over one another into an overlapping relationship. By way of illustration, FIG. 1 shows, in dashed lines, the first portion 120 of the release liner 104 being folded towards the patch 102 and the second portion 122 of the release liner 104.

In some embodiments, the fold and/or hinge 125 can be an integral hinge (or a "living hinge") formed in the release liner material. In some embodiments, first portion 120 and the second portion 122 of the release liner can be almost entirely separated, for example, along a cut or line of separation 127 between the first portion 120 and the second portion 122 that can be formed when the release liner 104 is formed (e.g., die cut). However, in such embodiments, as shown in FIGS. 1, 2 and 4, the release liner 104 can further include at least one uncut point 124 that can serve as an anchor point to allow the first portion 120 and the second portion 122 to remain coupled together during manufacturing, packaging, and storage. The uncut points 124 can be very small to facilitate separation of the first portion 120 and the second portion 122 during application of the patch 102 to the skin or other intended residence. The uncut points 124 can form the fold and/or hinge 125 which allows the release liner 104 to be folded. The fold and/or hinge 125 (i.e., the uncut points 124 in the embodiment of FIGS. 1-5) can also ensure proper alignment of the first portion 120 and the second portion 122 with the patch 102. As an example, in converting ~50 cm$^2$ patches on a 0.005"-(0.01 cm)-thick release liner, two 0.015" (0.04 cm) uncut points 124 were appropriate to allow the proper balance of ease of folding of the release liner 104 with adequate hinge strength to keep the folded release liner 104 unitized during converting and packaging.

The uncut points 124 are an example of a means for providing a release liner 104 that includes an integrally formed first portion 120 and the second portion 122. However, it should be understood that the first portion 120 and the second portion 122 can instead be coupled together via a variety of means, including but not limited to, adhesives, cohesives, crimps, welding (e.g., sonic (e.g., ultrasonic) welding), any thermal bonding technique (e.g., heat and/or pressure applied to one or both of the components to be coupled), being integrally formed, other suitable coupling means, or combinations thereof.

As such, in the embodiment illustrated in FIGS. 1-5, the first portion 120 and the second portion 122 can be folded over one another via the cut 127 therebetween but can remain coupled together via the at least one uncut point 124, such that the first portion 120 and the second portion 122 do not significantly move relative to one another during manufacturing, packaging, and storage, but can be easily separated when desired (i.e., during removal of the adhesive patch assembly 100 from the pouch 101 and/or application of the patch 102).

As shown in FIGS. 1-5, in some embodiments, the first portion 120 can be folded over the backing 110 (i.e., the first major surface 114 of the backing 110) of the patch 102, and the second portion 122 can be positioned to underlie the skin-contact adhesive 112 of the patch 102, such that the skin-contact adhesive 112 is releasably adhered to the second portion 122 of the release liner 104. In such embodiments, the second portion 122 of the release liner 104 can function as the "primary liner," and the first portion 120 of the release liner 104 can function as the "cover liner" or the "overlay liner," where the first portion (or overlay liner) 120 remains coupled to the second portion (or primary liner) 122 during manufacturing, packaging and storage, and can be removed from the second portion 122 when the patch 102 is to be used. As described above, the first portion 120 of the release liner 104 remains at least partially coupled to the second portion 122 of the release liner 104 during packaging and storage, such that should any cold flow or migration of the skin-contact adhesive 112 occur (e.g., during packaging and/or storage), the first portion (or cover liner) 120 of the release liner 104 will remain in position over the patch 102 and the second portion 122 of the release liner 104 to inhibit the skin-contact adhesive 112 from adhering to any pouch or packaging material, which may inhibit removal of the patch 102 from its package and/or proper application of the patch 102.

In some embodiments, as shown in FIGS. 1-5, the first portion 120 and the second portion 122 can generally have the same overall shape, size and area, and when folded, the first portion 120 and the second portion 122 of the release liner 104 can extend on all sides beyond a periphery of the patch 102. Such relative sizing between the patch 102 and the release liner 104 can ensure that even if the skin-contact adhesive 112 should flow (e.g., cold flow) during manufacturing, packaging, storage and/or shipment, the skin-contact adhesive 112 does not come into contact with, or adhere to, the pouch 101 or packaging material within which the adhesive patch assembly 100 is packaged. The extent to which the release liner 104 extends beyond the periphery of the patch 102 can depend on the particular patch 102 and skin-contact adhesive 112 employed, but at least about ⅛ inch (~0.3 cm) or ¼ inch (~0.6 cm) can be a useful distance between the periphery of the patch 102 and the periphery of the first portion 120 and the second portion 122 of the release liner 104 when the release liner 104 is folded about the patch 102.

By way of example only, in the embodiment illustrated in FIGS. 1-5, the second portion 122 of the release liner 104 is shown with a protrusion 123 in one corner, in the form of a decreased corner radius relative to the other liner corners. This protrusion 123 facilitates opening, or separation of the first portion 120 and the second portion 122 of the release liner 104 when desired, i.e., during application of the patch 102. The first portion 120 can then be torn from the second portion 122 of the release liner 104 and discarded.

By way of further example, in the embodiment illustrated in FIGS. 1-5, the release liner 104 can include a first dimension $L_1$ (e.g., length, see FIG. 2) that is at least twice a first dimension $L_2$ (e.g., length) of the patch 102 that generally extends in the same direction, such that the release liner 104 is double the length of a standard primary liner, and includes two halves (i.e., the first portion 120 and the second portion 122) that can be doubled over one another about the patch 102 to fully envelope the patch 102 and still extend on all sides beyond the periphery of the patch 102. The release liner 104 can further include a second dimension $D_1$ (e.g., width, diameter, etc.) that is greater than a second dimension $D_2$ (e.g., width, diameter, etc.) of the patch 102 that generally extends in the same direction, such that the release liner 104 extends beyond the edges of the patch 102.

In some embodiments, the area of the release liner 104, when in its folded configuration, can be at least about 1.05× (or "1.05 times") larger than the area of the patch 102, in some embodiments, at least about 1.2× larger, and in some embodiments, at least about 1.5× larger. In some embodiments, the area of the release liner 104, when in its folded configuration, can be no greater than about 2× larger than the area of the patch 102, in some embodiments, no greater than about 5× larger, and in some embodiments, no greater than about 10× larger. In some embodiments, area of the release liner 104, when in its folded configuration, relative to the area of the patch 102, can range from about 1.05× to about 1.2×, in some embodiments, from about 1.05× to about 2×, in some embodiments, from about 1.05× to about 5×, and in some embodiments, from about 1.05× to about 10×.

The release liner 104 includes a first major surface 130 and a second major surface 132 opposite the first major surface 130. At least the first major surface 130 can be configured to release the skin-contact adhesive 112 of the patch 102, or to present release characteristics relative to the skin-contact adhesive 112. As shown in FIGS. 1-5 (e.g., see FIGS. 3 and 5), the first major surface 130 is the surface of the first portion 120 and the second portion 122 of the release liner 104 that faces, is presented to, or is exposed to, the patch 102.

In addition, in some embodiments, the first major surface 114 (i.e., the surface opposite the skin-contact adhesive 112) of the backing 110, as well as at least portions of any other layers of the patch 102, can also be configured to release the skin-contact adhesive 112 of the patch 102, or to present release characteristics relative to the skin-contact adhesive 112.

As a result of the above release characteristics, even if cold flow of the skin-contact adhesive 112 should occur during storage and/or shipment of the adhesive patch assembly 110, the skin-contact adhesive 112 will not adhere, or will not adhere well, and will be easily removed from, the first major surface 130 of the release liner 104 and the first major surface 114 of the backing 110.

A surface that is "configured to release the skin-contact adhesive 112" or "configured to present release characteristics relative to the skin-contact adhesive 112" is a surface that may have a surface energy that is less than that of the skin-contact adhesive 112, such that the skin-contact adhesive 112 does not adhere or does not adhere well to the surface. Generally, "low surface energy" surfaces (i.e., low, relative to a particular adhesive) or surfaces that present "release characteristics" do not allow the adhesive to "wet out" the surface, so that strong adhesion does not occur between the adhesive and the surface with the low surface energy. Such low energy surfaces can be provided by a variety of materials (e.g., polyolefins), or such low energy surfaces can be provided by a surface modification, e.g., by coating the surface with a release agent. Examples of various materials and release agents that can be employed in the release liner 104 are described in greater detail below. In addition, or alternatively to the relative surface energies described above, in some embodiments, a surface "configured to release the skin-contact adhesive 112" can have surface contours, such as a microreplicated pattern, that serves to minimize contact between the surface and the skin-contact adhesive.

The phrase "does not adhere well," or variations thereof, can generally refer to the adhesive, e.g., the skin-contact adhesive 112, having a 90 degree peel strength, at least initially, of less than about 50 g, in some embodiments, less than about 30 g, and in some embodiments, less than about 20 g, when a 1-inch-(2.54 cm)-wide strip of the patch 102 having the skin-contact adhesive 112 is peeled from another surface, such as the first major surface 130 of the release liner 104.

The phrase "adheres well," or variations thereof, can generally refer to the adhesive, e.g., the skin-contact adhesive 112, having a 90 degree peel strength, at least initially, of at least about 500 g, in some embodiments, at least about 800 g, and in some embodiments, at least about 1000 g (1 kg), when a 1-inch-(2.54 cm)-wide strip of the patch 102 having the skin-contact adhesive 112 is peeled from another surface, such as the skin to which the skin-contact adhesive 112 is configured to be adhered.

As shown in FIG. 5, when the release liner 104 is folded about the patch 102, the patch 102 is located between the first portion 120 and the second portion 122 of the release liner 104 with the skin-contact adhesive 112 of the patch 102 (releasably) adhered to the second portion 122, such that the second portion 122 underlies the patch 102, and the first portion 120 overlies the backing 110 of the patch 102. Because the first major surface 130 of the first portion 120 and the second portion 122 faces the patch 102, there is no coupling or adhesion between the backing 110 and the first portion 120 of the release liner 104, unless cold flow of the skin-contact adhesive 112 occurs, in which case the skin-contact adhesive 112 may migrate out from within the periphery of the backing 110, and the skin-contact adhesive 112 may at least partially adhere (i.e., releasably) to the first portion 120 of the release liner 104 as well. However, in order to solve the problems that may occur as a result of cold flow of the skin-contact adhesive 112, the first major surface 130 presents release characteristics relative to the skin-contact adhesive 112 and generally does not include any adhesive or means for adhering to the patch 102. Rather, only the patch 102 includes an adhesive—i.e., the skin-contact adhesive 112.

In some embodiments, the release characteristics can be coextensive with the first major surface 130, such that any portion of the first major surface 130 will function as a release liner for the skin-contact adhesive 112. Said another way, in embodiments in which the release characteristics are coextensive with the first major surface 130, the release characteristics can extend across the entire first major surface 130 (or "release side") of the release liner 104, so there are no, or minimal, areas of non-release that face the patch 102.

In some embodiments, the coefficient of adhesion (or adhesion, or adhesive strength) between the first major surface 130 of the release liner 104 and the backing 110 (e.g., the first major surface 114 of the backing 110) of the patch 102 is less than the coefficient of adhesion (or adhesion, or adhesive strength) between the first major surface 130 of the release liner 104 and the skin-contact adhesive 112 of the patch 102. That is, the skin-contact adhesive 112 can be adhered, at least weakly, to the second portion 122 of the release liner 104, however, the backing 110 and the first major surface 130 of the first portion 120 of the release liner 104 are generally configured not to adhere to one another. As described above, during storage and/or shipment of the finished adhesive patch assembly 100, cold flow of the skin-contact adhesive 112 may occur that causes at least a portion of the patch 102 to become at least partially (or weakly) adhered to the first major surface 130 of the first portion 120 of the release liner 104. However, neither the release liner 104 nor the backing 110 are constructed to adhere to one another.

The relative coefficients of adhesion between layers within the adhesive patch assembly 100 will generally be ordered as follows, from weakest to strongest: (1) the coefficient of adhesion between the backing 110 and the first major surface 130 of the release liner 104; (2) the coefficient of adhesion between the first major surface 130 of the release liner 104 and the skin-contact adhesive 112, which in the embodiment illustrated in FIGS. 1-5, will generally be weakly adhered to the first major surface 130 of the second portion 122 of the release liner 104; and (3) the coefficients of adhesion between the skin-contact adhesive 112 and skin to which the skin-contact adhesive 112 is configured to be adhered and between the backing 110 (or other layers of the patch 102) and the skin-contact adhesive 112 (e.g., such that the patch 102 cannot easily become disassembled during manufacturing, packaging, storage and/or use). Said another way, the coefficient of adhesion (1) is generally less than the coefficient of adhesion (2), which is generally less than either of the coefficients of adhesion (3). Alternatively, the coefficients of adhesion (3) are each generally greater than the coefficient of adhesion (2), which is generally greater than the coefficient of adhesion (1).

Such a configuration of relative coefficients of adhesion between the layers and elements of the adhesive patch assembly 100 can ensure that (i) patch 102 can be easily removed from between the first portion 120 and the second portion 122 of the release liner 104 when desired, (ii) the patch 102 will remain intact (i.e., that the backing 110 and the skin-contact adhesive 112 will not delaminate), and (iii) the patch 102 will properly adhere to the desired surface (i.e., skin).

In some embodiments, the release liner 104 includes a monolithic or non-laminate construction, such that the release liner 104 is formed from one sheet of material and does not include any additional layers, adhesives, etc.

As shown in FIGS. 1-5, in some embodiments, the second portion 122 of the release liner 104 (or the "primary liner") can include one or more slits 140 that can be formed when the release liner 104 is formed (e.g., die cut). Such slit(s) 140 can be used to facilitate separation of the second portion 122 of the release liner 104 and the patch 102 during application of the patch 102. As is known in the art, the second portion 122 of the release liner 104 can also include a tab (e.g., adjacent the slit(s) 140, as shown in dashed lines and represented by numeral 141 in FIG. 1) to further facilitate peeling the release liner 104 from the patch 102, or vice versa. Such slit(s) 140 can be straight, angled, curved, wavy, etc., or combinations thereof. As a result of the slit 140, the illustrated second portion 122 of the release liner 104 itself actually includes two separate sections, for example, that can be separated from the patch 102 sequentially during application of the patch 102.

As shown in FIGS. 3 and 5 by way of example only, in some embodiments, the patch 102 can further include one or more optional additional layers 118 between the backing 110 and the skin-contact adhesive 112, such that the skin-contact adhesive 112 is still coupled, but not directly coupled, to the second major surface 116 of the backing 110. One such layer 118 is shown by way of example in FIGS. 3 and 5. Such additional layer(s) 118 may include, for example, tie layers that enhance the coupling between the backing 110 and the skin-contact adhesive 112; a drug reservoir comprising an active ingredient (or "active," or "active agent," or "medicament"—e.g., a drug); a skin-penetration enhancer; a permeation rate-controlling membrane; a protective layer that inhibits interaction between an active ingredient and the backing 110; or combinations thereof.

In some embodiments, the adhesive patch assembly 100 (or the release liner 104), when in the folded configuration, can have a surface area of at least about 0.5 cm$^2$, in some embodiments, at least about 1 cm$^2$, and in some embodiments, at least about 2 cm$^2$. In some embodiments, the adhesive patch assembly 100 (or the release liner 104) can have an area of no greater than about 220 cm$^2$, in some embodiments, no greater than about 150 cm$^2$, and in some embodiments, no greater than about 50 cm$^2$. In some embodiments, the area of the adhesive patch assembly 100 (or the release liner 104) in the folded configuration can range from about 0.5 cm$^2$ to about 200 cm$^2$; in some embodiments, from about 1 cm$^2$ to about 150 cm$^2$; and in some embodiments, from about 2 cm$^2$ to about 50 cm$^2$.

In some embodiments, the release liner 104 can be dimensioned to accommodate multiple patches 102. For example, in some embodiments, two different patches 102 (e.g., which can include the same or a different active ingredient) may be desired to be applied at the same time. In such combination doses, for example, more than one patch 102 can be located in the same adhesive patch assembly 100, located between the first portion 120 and the second portion 122.

The backing 110 of the patch 102 can be formed of a variety of materials, including flexible films. Examples of flexible films that can be employed as a backing 110 for the patch 102 can include those made from polymer films such as polypropylene; polyethylene, particularly low density polyethylene, linear low density polyethylene, metallocene polyethylenes, and high density polyethylene; polyvinyl chloride; polyester (e.g., polyethylene terephthalate); polyvinylidene chloride; ethylene-vinyl acetate (EVA) copolymer; polyurethane; cellulose acetate; and ethyl cellulose. Coextruded multilayer polymeric films can also be suitable, such as those described in U.S. Pat. No. 5,783,269 (Heilmann et al.), the disclosure of which is incorporated herein by reference. Backings 110 that are layered such as polyethylene terephthalate-aluminum-polyethylene composites and polyethylene terephthalate-EVA composites can also be suitable. Foam tape backings, such as closed cell polyolefin films used in 3M™ 1777 Foam Tape and 3M™ 1779 Foam Tape (available from 3M Co., St. Paul, Minn.) can also be suitable. Polyethylenes, polyethylene blends, polyethylene composites, and polyurethanes can be preferred polymer films. Polyethylenes and polyurethanes can be optimal polymer films. In one embodiment, the backing 110 can be a translucent or transparent film. Additives may also be added to films used as a backing 110, such as tackifiers, plasticizers, colorants, and anti-oxidants.

The patches 102 of the present disclosure, and particularly the backings 110 (e.g., the first major surface 114 of the backing 110) may also include a release agent coating or a low adhesion coating, as described above. One example of a suitable low adhesion coating can be coated as a solution of polyvinyl N-octadecyl carbamate and a blend of silicone resins, as described in U.S. Pat. No. 5,531,855 (Heinecke et al.), the disclosure of which is incorporated herein by reference.

In some embodiments, the thickness of the backing 110 (or other optional additional layers in the patch 102) can be at least about 10 μm, in some embodiments, at least about 20 μm, and in some embodiments, at least about 40 μm. In some embodiments, the thickness of the backing 110 can be less than about 2 mm (0.07874 inch), in some embodiments, less than about 1 mm (0.03937 inch), and in some embodiments, less than about 150 microns (5906 microinches).

The skin-contact adhesive 112 is generally a pressure-sensitive adhesive, and particularly is a pressure-sensitive adhesive that is capable of securely but releasably adhering or bonding to skin (e.g., mammalian skin). The skin-contact adhesive 112 is also generally safe and non-toxic. Skin-contact adhesive layers will generally be selected according to the desired end use of the patch 102. In some embodiments, the patch 102 can include more than one skin-contact adhesive 112. Where the patch 102 comprises more than one skin-contact adhesive layer 112, each skin-contact adhesive layer 112 may be selected independently of each other with regard to material and thickness used. Examples of suitable adhesives include acrylates, silicones, polyisobutylenes, synthetic rubber, natural rubber, and copolymers and mixtures thereof. Acrylates and silicones can be preferred skin-contact adhesives 112. In general, the skin-contact adhesive 112 should cause little or no irritation or sensitization of the skin during the intended wear period.

In some embodiments, the skin-contact adhesive 112 can be an acrylate (or methacrylate) copolymer. Acrylates will typically have an inherent viscosity greater than about 0.2 dL/g and will comprise one or more polymerized primary monomers and optionally one or more polar comonomers. Primary monomers suitable for use include alkyl acrylates containing 4 to 12 carbon atoms in the alkyl group and alkyl methacrylates containing 4 to 12 carbon atoms in the alkyl group. Examples of suitable alkyl acrylates and methacrylates include n-butyl, n-pentyl, n-hexyl, isoheptyl, n-nonyl, n-decyl, isohexyl, 2-ethyloctyl, isooctyl and 2-ethylhexyl acrylates and methacrylates. In some embodiments, the alkyl acrylates can include isooctyl acrylate, 2-ethylhexyl acrylate, n-butyl acrylate, and cyclohexyl acrylate. Polar monomers suitable for use can include those having hydroxyl, amide, or carboxylic, sulfonic, or phosphonic acid functionality. Representative examples include acrylamide, methacrylamide, N-vinyl-2-pyrrolidone, 2-hydroxyethylacrylate, 2-hydroxyethylmethacrylate, hydroxypropylacrylate, acrylic acid, methacrylic acid, pyrrolidonyl ethyl acrylate, and alkoxyethyl acrylates, such as 2-carboxyethylacrylate. In some embodiments, the amount by weight of polar monomer will not exceed about 40% of the total weight of all monomers in order to avoid excessive firmness of the final PSA product. Typically, polar monomer can be incorporated to the extent of about 1% to about 20% by weight. In some embodiments, the polar monomer can be acrylamide.

In some embodiments, the acrylate copolymer can comprise the reaction product of primary and polar monomers and additional optional monomers which, when present, are included in the polymerization reaction in quantities that will not render the adhesive composition non-tacky. The optional additional monomers may be added, for example, to improve performance, reduce cost, or for other purposes. Examples of such optional monomers include vinyl esters, such as vinyl acetate, vinyl chloride, vinylidene chloride, styrene, and macromonomers copolymerizable with the other monomers. Suitable macromonomers include polymethylmethacrylate, styrene/acrylonitrile copolymer, polyether, and polystyrene macromonomers. Examples of useful macromonomers and their preparation are described in U.S. Pat. No. 4,693,776 (Krampe et al.), the disclosure of which is incorporated herein by reference.

Silicone or polysiloxane pressure-sensitive adhesives include pressure-sensitive adhesives which are based on two major components: a polymer, or gum, and a tackifying resin. The polysiloxane adhesive can be prepared by cross-linking the gum, typically a high molecular weight polydiorganosiloxane, with the resin, to produce a three-dimensional silicate structure, via a condensation reaction in an appropriate organic solvent. The ratio of resin to polymer can be adjusted in order to modify the physical properties of polysiloxane adhesives. Use of capped (or amine-compatible) polysiloxanes can, in some embodiments, be preferred so as to increase drug stability and reduce degradation. Further details and examples of silicone pressure-sensitive adhesives which can be useful are described in the U.S. Pat. No. 4,591,622 (Blizzard et al.); U.S. Pat. No. 4,584,355 (Blizzard et al.); U.S. Pat. No. 4,585,836 (Homan et al.); and U.S. Pat. No. 4,655,767 (Woodard et al.). Suitable silicone pressure-sensitive adhesives are commercially available and include the silicone adhesives sold under the trademarks BIO-PSA® by Dow Corning Corporation, Medical Products, Midland, Mich.

Further description of suitable adhesives may be found in U.S. Pat. No. 5,656,286 (Miranda et al.), U.S. Pat. No. 5,223,261 (Nelson et al.), and U.S. Pat. No. 5,380,760 (Wendel et al.), the disclosures of which are incorporated herein by reference. In some embodiments, the thickness of the skin-contact adhesive 112 can be at least about 10 µm, in some embodiments, at least about 20 µm, and in some embodiments, at least about 40 µm. In some embodiments, the thickness of the skin-contact adhesive 112 can be less than about 2 mm (0.07874 inch), in some embodiments, less than about 1 mm (0.03937 inch), and in some embodiments, less than about 150 microns (5906 microinches).

In some embodiments, active ingredients or agents (e.g., drugs) can be employed in the patch 102 (e.g., in the skin-contact adhesive 112 or in one or more additional layers in the patch 102). Examples of pharmaceutically active agents (also referred to as "drugs") that can be included in the reservoir are capable of local or systemic effect when administered to the skin. Some examples include, buprenorphine, clonidine, diclofenac, estradiol, granisetron, isosorbide dinitrate, levonorgestrel, lidocaine, methylphenidate, nicotine, nitroglycerine, oxybutynin, rivastigmine, rotigotine, scopolamine, selegiline, testosterone, tulobuterol, and fentanyl, which are commercially available in the form of transdermal devices. Other examples include antiinflammatory drugs, both steroidal (e.g., hydrocortisone, prednisolone, triamcinolone) and nonsteroidal (e.g., naproxen, piroxicam); bacteriostatic agents (e.g., chlorhexidine, hexylresorcinol); antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin); antiprotazoals (e.g., metronidazole); antifungals (e.g., nystatin); coronary vasodilators; calcium channel blockers (e.g., nifedipine, diltiazem); bronchodilators (e.g., theophylline, pirbuterol, salmeterol, isoproterenol); enzyme inhibitors such as collagenase inhibitors, protease inhibitors, acetylcholinesterase inhibitors (e.g., donepezil), elastase inhibitors, lipoxygenase inhibitors (e.g., A64077), and angiotensin converting enzyme inhibitors (e.g., captopril, lisinopril); other antihypertensives (e.g., propranolol); leukotriene antagonists (e.g., ICI204,219); anti-ulceratives such as H2 antagonists; steroidal hormones (e.g., progesterone); antivirals and/or immunomodulators (e.g., 1-isobutyl-1H-imidazo[4,5-c]quinolin-4-amine, 1-(2-hydroxy-2-methylpropyl)-1H-imidazo[4,5-c]quinolin-4-amine, N-[4-(4-amino-2-ethyl-1H-imidazo[4,5-c]quinolin-1-yl)butyl]methanesulfonamide, and acyclovir); local anesthetics (e.g., benzocaine, propofol, tetracaine, prilocaine); cardiotonics (e.g., digitalis, digoxin); antitussives (e.g., codeine, dextromethorphan); antihistamines (e.g., diphenhydramine, chlorpheniramine, terfenadine); narcotic analgesics (e.g., morphine, fentanyl citrate, sufentanil, hydromorphone hydrochloride); peptide hormones (e.g., human or animal growth hormones, LHRH, parathyroid hormones); cardioactive products such as atriopeptides; antidiabetic agents (e.g., insulin, exanatide); enzymes (e.g., anti-plaque enzymes, lysozyme, dextranase); antinauseants; anticonvulsants (e.g., carbamazine); immunosuppressives (e.g., cyclosporine); psychotherapeutics (e.g., diazepam); sedatives (e.g., phenobarbital); anticoagulants (e.g., heparin, enoxaparin sodium); analgesics (e.g., acetaminophen); antimigraine agents (e.g., ergotamine, melatonin, sumatripan, zolmitriptan); antiarrhythmic agents (e.g., flecainide); antiemetics (e.g., metaclopromide, ondansetron, granisetron hydrochloride); anticancer agents (e.g., methotrexate); neurologic agents such as anxiolytic drugs; hemostatics; antiobesity agents; dopamine agonists (e.g., apomorphine); GnRH agonists (e.g., leuprolide, goserelin, nafarelin); fertility hormones (e.g., hCG, hMG, urofollitropin); interferons (e.g., interferon-alpha, interferon-beta, pegylated interferon-alpha); and the like, as well as pharmaceutically acceptable salts and esters thereof. The amount of drug that constitutes a therapeutically effective amount can be readily determined by those skilled in the art with due consideration of the particular drug, the particular carrier, and the desired therapeutic effect.

In some embodiments, drugs that are of a large molecular weight may be delivered transdermally. Increasing molecular weight of a drug typically causes a decrease in unassisted transdermal delivery. Examples of such large molecules include proteins, peptides, nucleotide sequences, monoclonal antibodies, vaccines, polysaccharides, such as heparin, and antibiotics, such as ceftriaxone. Examples of suitable vaccines include flu vaccine, Lyme disease vaccine, rabies vaccine, measles vaccine, mumps vaccine, chicken pox vaccine, small pox vaccine, hepatitis vaccine, pertussis vaccine, rubella vaccine, diphtheria vaccine, encephalitis vaccine, yellow fever vaccine, recombinant protein vaccine, DNA vaccines, polio vaccine, therapeutic cancer vaccine, herpes vaccine, pneumococcal vaccine, meningitis vaccine, whooping cough vaccine, tetanus vaccine, typhoid fever vaccine, cholera vaccine, tuberculosis vaccine, and combinations thereof. The term "vaccine" thus includes, without limitation, antigens in the forms of proteins, polysaccharides, oligosaccharides, or weakened or killed viruses. Additional examples of suitable vaccines and vaccine adjuvants are described in U.S. Publication No. 2004/0049150 (Dalton et al.), the disclosure of which is hereby incorporated by reference.

In some embodiments, the patch 102 can include a drug reservoir (or drug reservoir layer), for example, which can form at least a portion of an optional additional layer in the patch 102. In some embodiments, such a drug reservoir can be located between the backing 110 and the skin-contact adhesive 112. The size of such a drug reservoir can be suitable to deliver a selected amount of drug through the skin. Generally, the reservoir can have a surface area at least about 0.5 cm$^2$, in some embodiments, at least about 1.0 cm$^2$, and in some embodiments, at least about 5 cm$^2$. Generally, the reservoir can have a surface area of less than about 100 cm$^2$, and in some embodiments, less than about 40 cm$^2$. The reservoir can have the same surface area as the patch 102, but it will typically be smaller in surface area than the patch 102. In some embodiments, the reservoir can be centrally placed within the patch 102, such that it can be surrounded on all sides by a rim of skin-contact adhesive 112 that can help to secure the drug reservoir in place on a skin surface. The thickness of the drug reservoir can be at least about 10 μm, in some embodiments, at least about 20 μm, and in some embodiments, at least about 40 μm. In some embodiments, the drug reservoir thickness can be less than about 2 mm (0.07874 inch), in some embodiments, less than about 1 mm (0.03937 inch), and in some embodiments, less than about 150 microns (5906 microinches).

In some embodiments, the drug reservoir can be provided in the form of a transdermal patch adhered to the skin-contact adhesive 112 of the patch 102. Any transdermal patch suitable for the continuous transdermal delivery of a therapeutically effective amount of an appropriate medicament may be used. Suitable transdermal patches include gelled or liquid reservoirs, such as in U.S. Pat. No. 4,834,979 (Gale), so-called "reservoir" patches; patches containing matrix reservoirs attached to the skin by an adjacent adhesive layer, such as in U.S. Pat. No. 6,004,578 (Lee et al.), so-called "matrix" patches; and patches containing PSA reservoirs, such as in U.S. Pat. No. 6,365,178 (Venkateshwaran et al.), U.S. Pat. No. 6,024,976 (Miranda et al.), U.S. Pat. No. 4,751,087 (Wick) and U.S. Pat. No. 6,149,935 (Chiang et al.), so-called "drug-in-adhesive" patches, the disclosures of which are hereby incorporated by reference. In some embodiments, the reservoir can have an impermeable backing that substantially or fully inhibits migration of drug and/or excipients from the reservoir into the skin-contact adhesive 112 of the patch 102. Selection of an appropriate impermeable backing will depend upon the composition of the reservoir and one skilled in the art may readily determine a suitable backing by testing patches for drug and/or excipient migration. Typical impermeable barriers include films containing one or more polyethylene terephthalate layers and/or an aluminum barrier layer. In some embodiments, the impermeable backing can function to limit oxygen and/or water vapor permeation. Examples of impermeable backings can include films having plasma-deposited amorphous glass layers, such as described in WO 2011/066493 (Kluge et al. to 3M), and films having translucent inorganic barrier layers, such as described in US 2004/202708 (Roehrig et al. to 3M).

In some embodiments, the drug reservoir can be provided in the form of a matrix layer containing drug, the matrix layer being adhered to the skin-contact adhesive 112 of the patch 102. Such a matrix can be an adhesive layer and can include any of the adhesives described above. Alternatively, the matrix layer can be non-adhesive or weakly adhesive and rely upon a surrounding rim of skin-contact adhesive 112 to secure the patch 102 in place and keep the drug reservoir in contact with the skin surface.

In another embodiment, the drug reservoir can be provided in the form of solid particles embedded on the surface or within the skin-contact adhesive 112 of the patch 102. In particular, these particles may be hydrophilic, so that contact with aqueous fluid exposed at the surface of the treated skin will cause them to dissolve or disintegrate, thus releasing drug into the skin.

In some embodiments, the drug reservoir can be provided within the skin-contact adhesive 112 of the patch 102. The drug can be mixed with the skin-contact adhesive 112 prior to forming the patch 102 or it may be applied to the skin-contact adhesive 112 of the patch 102 in a separate process step. Examples of suitable methods for applying drug to an adhesive layer may be found in U.S. Patent Application Publication No. 2003/054025 (Cantor et al.) and U.S. Pat. No. 5,688,523 (Garbe et al.), the disclosures of which are hereby incorporated by reference.

Release liners are available from a variety of manufacturers in a wide variety of proprietary formulations. Those skilled in the art will normally test those liners in simulated use conditions against an adhesive of choice to arrive at a product with the desired release characteristics. The materials used to supply the liners for the patches 102 of the present disclosure can be substantially more rigid than the backing 110, but this need not be the case. Liners which can be suitable for use in the adhesive patch assemblies 100 of the present disclosure can be made of kraft papers, polyethylene, polypropylene, polyester or composites of any of these materials. The liners material can be coated with release agents or low adhesion coatings, such as fluorochemicals or silicones. For example, U.S. Pat. No. 4,472,480 (Olson), the disclosure of which is hereby incorporated by reference, describes low surface energy perfluorochemical liners. The liners can be papers, polyolefin films, or polyester films coated with silicone release materials. Examples of commercially available silicone coated release papers are POLYSLIK® silicone release papers available from Loparex (Willowbrook, Ill.).

In some embodiments, the length of time that the patch 102 remains on the skin and in a delivering relationship may be an extended time, for example, from about 12 hours to about 14 days. In some embodiments, the duration of time that the reservoir remains in a delivering relationship can be about 1 day (i.e., daily dosing), about 3 to 4 days (i.e., bi-weekly dosing), or about 7 days (i.e., weekly dosing).

In some embodiments, the duration of time that the patch 102 remains in a delivering relationship may be relatively short, for example from about 1 minute to about 1 hour, in some embodiments, from about 5 minutes to about 40 minutes, and in some embodiments, from about 5 minutes to about 20 minutes.

Figure 6:
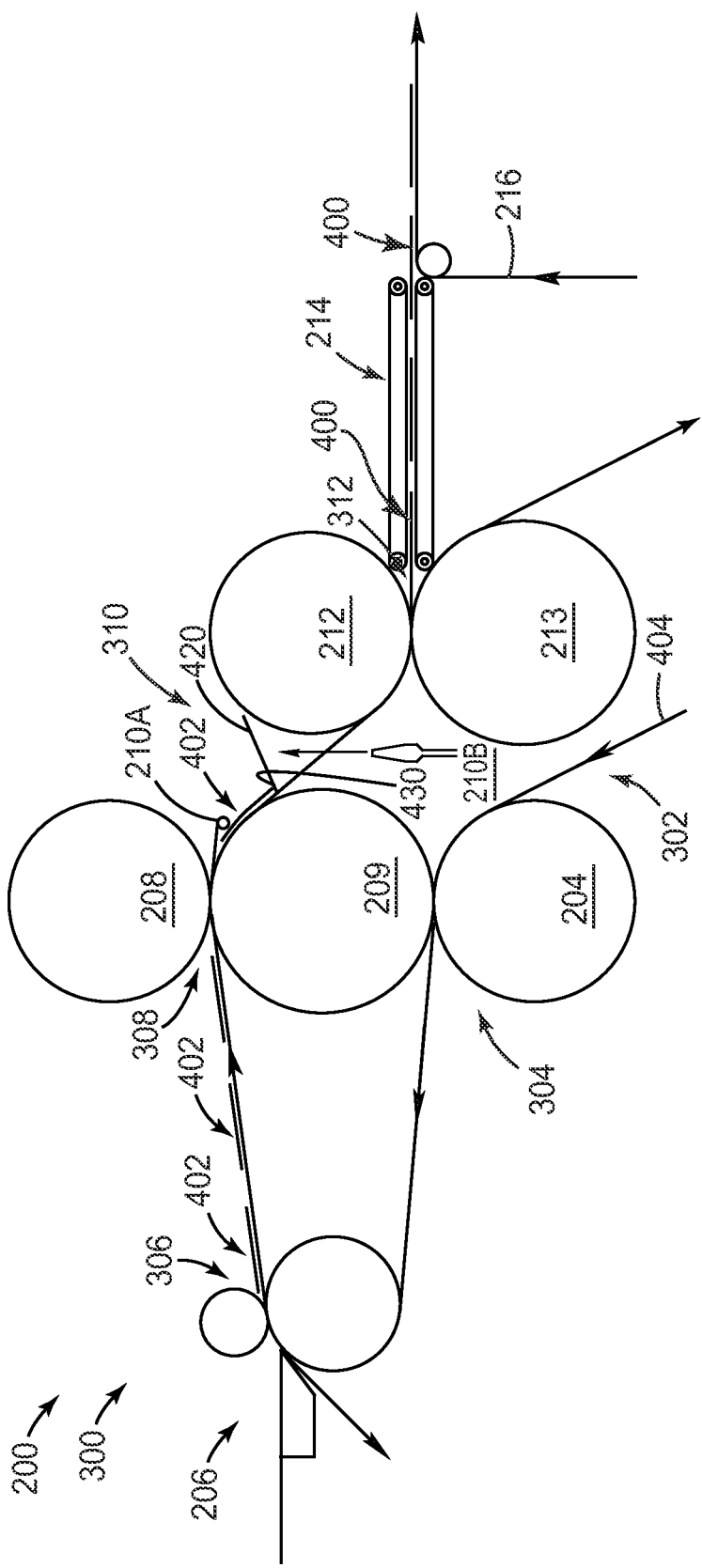
FIG. 6 is a schematic view of a system and method of making an adhesive patch assembly according to one embodiment of the present disclosure.

FIG. 6 illustrates a schematic view of a system 200 that can be used to make adhesive patch assemblies of the present disclosure. FIG. 6 also illustrates a method 300 of making adhesive patch assemblies of the present disclosure. FIGS. 7A-7F illustrate the products formed at various stages of the method 300 shown in FIG. 6.

FIGS. 7A-7F illustrate an adhesive patch assembly 400 according to another embodiment of the present disclosure, wherein like numerals represent like elements. The adhesive patch assembly of FIGS. 7A-7F share many of the same elements and features as the embodiment described above with respect to FIGS. 1-5. Reference is made to the description above accompanying FIGS. 1-5 for a more complete description of the features and elements (and alternatives to such features and elements) of the embodiment illustrated in FIGS. 7A-7F. Any of the features described above with respect to FIGS. 1-5 can be applied to the embodiments of FIGS. 7A-7F, and vice versa. In addition, as described below, the system 200 and the method 300 can also be used to make the adhesive patch assembly 100 of FIGS. 1-5. The adhesive patch assembly 400 is illustrated in FIGS. 7A-7F by way of example only to illustrate an additional embodiment of an adhesive patch assembly of the present disclosure.

Figure 7A:
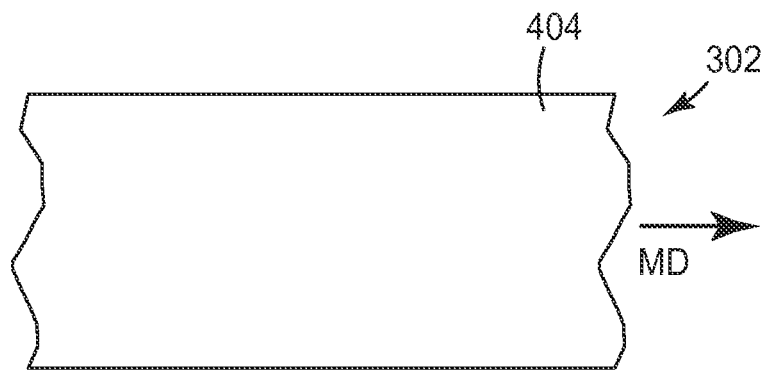
FIGS. 7A-7F illustrate the products formed at each step of the method of FIG. 6.
Figure 7B:
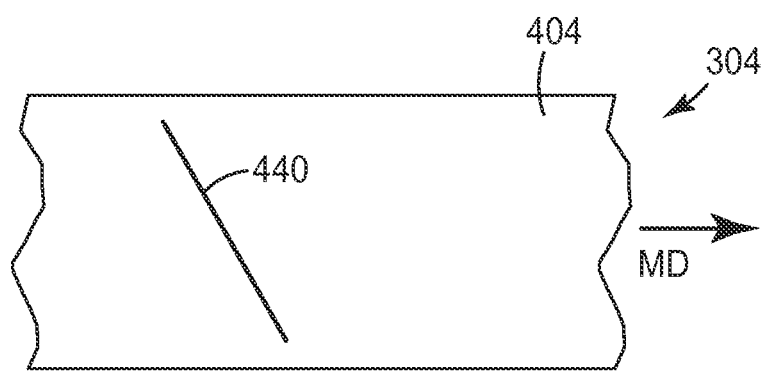

As shown in FIGS. 6 and 7A, at step 302 of the method, a web (i.e., a continuous web) of a release liner 404 can be fed into a series of rolls or rollers along a machine direction ("MD"), which is represented by the arrows in FIG. 6 and the arrow "MD" in FIGS. 7A-7E.

At step 304 (see FIGS. 6 and 7B), the release liner 404 can be cut (e.g., die-cut between a slit die 204 and a first anvil roll 209) to form one or more slits 440 (see FIG. 7B) in the release liner 404, and particularly, in a portion of the release liner 404 that will eventually form the second portion (or "primary liner") 422 of the release liner 404. The slit(s) 440 will eventually facilitate removal of the second portion 422 of the release liner 404 from the adhesive patch 402.

Figure 7C:
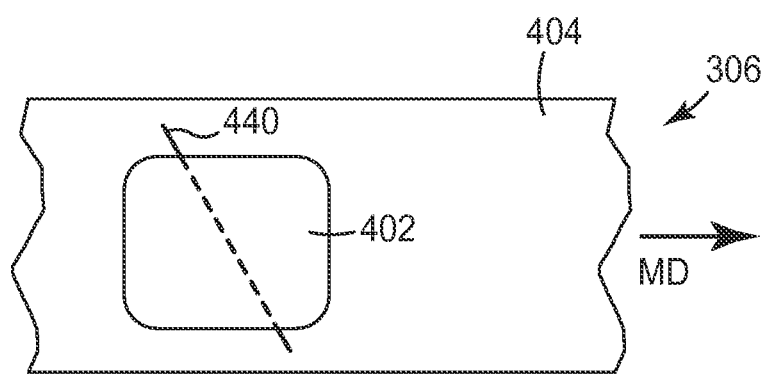

At step 306 (see FIGS. 6 and 7C), the patch 402 can be placed onto the release liner 404 over the slit(s) 440 at island placement station 206. As shown in FIG. 7C, the slit(s) 440 can be spaced out from one another on the release liner 404 in the MD to allow for later formation of the first portion 420 of the release liner 404. In addition, as shown, the patches 402 can be positioned over the slit(s) 440, can be generally centered across the width of the release liner 404, and can be spaced apart along the MD to allow for later formation of the first portion 420 of the release liner 404 that will be free of slits 440 and patches 402. While only one slit 440 and one patch 402 is shown in FIG. 7C for simplicity and clarity, the empty space on the release liner 404 adjacent the patch 402 makes it clear that another patch 402 is not placed immediately adjacent the patch 402 that is shown, in order to allow for the formation of the first portion 420 of the release liner 404.

As shown in FIG. 7C, the patches 402 can be spaced apart in such a way that the first portion 420 and the second portion 422 of the release liner 404 that will be formed are each dimensioned to accommodate the patch 402. That is, each portion 420, 422 of the release liner 404 can be dimensioned to accommodate at least one patch 402, so that the release liner 404 for one patch 402 has a first dimension (e.g., length) that is at least twice that of the patch 402.

Figure 7D:
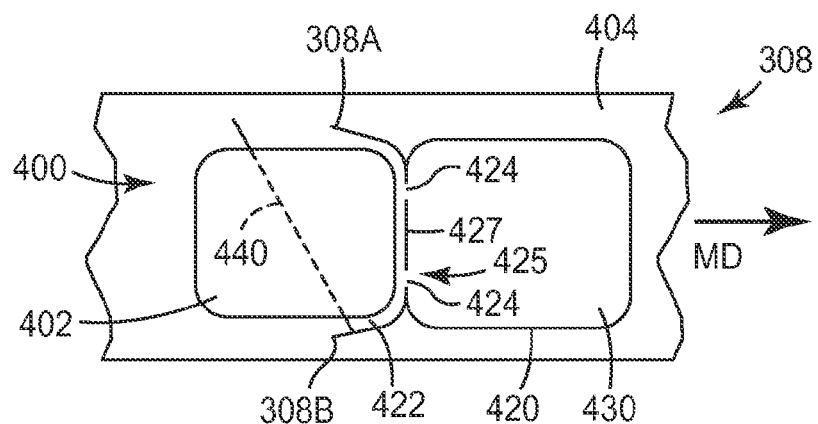
Figure 7E:
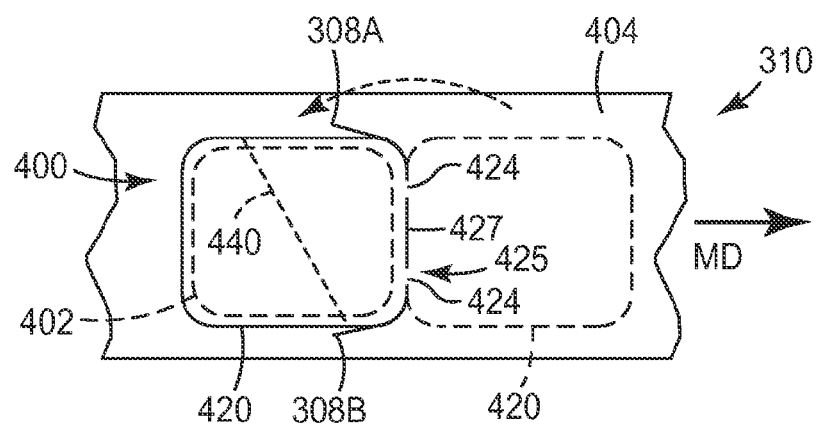

At step 308 (see FIGS. 6 and 7D), a portion of the release liner shape (shown in FIG. 7D) can be formed (e.g., die-cut) next to and at least partially around the patch 402 by a first liner die (e.g., rotary die) 208 (which can also be referred to as a "cover liner die") to form the first portion 420 and a portion of the second portion 422 of the release liner 404, which are separated from one another along a cut or line of separation 427, but which remain coupled together at one or more uncut points 424 (two are shown by way of example only). As such, the uncut points 424 form a hinge 425 about which the first portion 420 and the second portion 422 can be folded to overlap one another. As shown in FIG. 7D, the first portion 420 of the release liner 404 (or the "cover liner") leads in the MD. As further shown in FIG. 7D, in some embodiments, the cut(s) forming the first portion 420 of the release liner 404 can extend rearwardly and at least partially around the patch 402 to one or more termination points—a first termination point 308A and a second termination point 308B are shown by way of example only. The termination points 308A, 308B can be provided to form a portion of the second portion 422 of the release liner 404. As shown in FIG. 6 by way of example only, such a first partial shape of the release liner 404 can be formed by an interface between the first liner die 208 and the first anvil roll 209.

At step 310 (see FIGS. 6 and 7E), the release liner 404 can be folded to provide the patch 402 between the first portion 420 and what will be the second portion 422 of the release liner 404. As described above, the release liner 404 can be folded, such that a first major surface 430 (see FIGS. 6 and 7D) of the release liner 404 faces the patch 402 when the patch 402 is located between the first portion 420 and the second portion 422 of the release liner 404. The first portion 420 is shown unfolded in dashed lines, and folded in solid lines.

In one embodiment of the folding step, the leading edge of the first portion 420 of the release liner 404 exits the first liner die 208/first anvil roll 209 interface, and encounters a cross-web folding rod (or bar) 210A, or a compressed air nozzle 210B. In the example of the folding rod 210A, the folding rod 210A can be positioned such that the leading edge of the first portion 420 of the release liner 404 is farther from the rotary axis of the first anvil roll 209 than the folding rod 210A, thereby engaging the folding rod 210A in a manner which causes the first portion 420 of the release liner 404 to fold rearward as the web moves under the folding rod 210A. The termination points 308A and 308B can serve at least two purposes in this process, one of which is to keep the leading edge of the second portion 422 and the folded first portion 420 close enough to the axis of the first anvil roll 209 to avoid engagement with the folding rod 210A, and another is to maintain attachment of the second portion 422 of the release liner 404 and thereby, the entire adhesive patch assembly 400, to the web of the release liner 404 for transport through the folding process and to a second liner die 212 (which can also be referred to as a "primary liner die"), and a second anvil roll 213.

Alternatively, the first portion 420 can be folded by supplying a stream of air to the underside of the web with the compressed air nozzle 210B, lifting the first portion 420 into position to be folded by the second liner die 212. In some embodiments, a combination of the folding rod 210A and the nozzle 210B can be employed to fold the release liner 404.

Because in the illustrated method, the first portion 420 of the release liner 404 leads in the MD, the first portion 420 is folded over the second portion 422 and the patch 402. However, it should be understood that in some embodiments, the second portion 422 and the patch 402 can instead be folded over the first portion 420.

At step 312 (see FIG. 6 and FIG. 7F), a final cut (e.g., die cut) can be made by the second liner die 212 to form the second portion 422 of the release liner 404, and the leading edges of the adhesive patch assemblies 400 can be nipped by a set of belted conveyors 214, which propels the adhesive patch assemblies 400 onto a lower packaging foil 216. The web of release liner 404 is not shown in FIG. 7F.

Figure 7F:
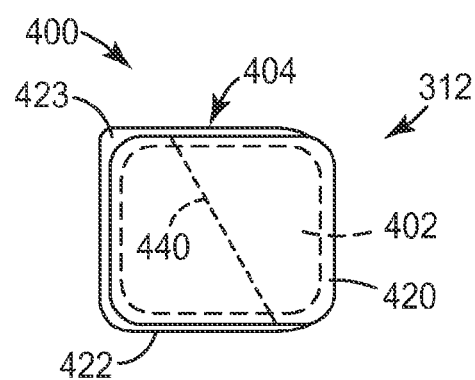

As shown in FIG. 7F, at least a portion of the final cut that is made to form the second portion 422 overlaps the previously formed first and second termination points 308A and 308B (see FIGS. 7D and 7E) to ensure that the second portion 422 is completely formed (i.e., cut) from the web of the release liner 404. As further shown in FIG. 7F, the area of the second portion 422 of the release liner 404 can be slightly larger than that of the first portion 420. While this need not be the case, such a configuration can inhibit the second liner die 212 from additionally cutting the edges of the first portion 420 when the second portion 422 is formed, because the first portion 420 will already be folded over when the second portion 422 is formed. In some embodiments, the gap between an outer edge of the first portion 420 and an outer edge of the second portion 422 can be at least about ⅛ inch (~0.3 cm).

The second portion 422 is also shown in FIG. 7F as including a corner 423 having a reduced radius that can be used to facilitate separating the first portion 420 and the second portion 422 of the release liner 404 during application of the patch 402. However, in embodiments in which the second portion 422 is slightly larger than the first portion 420, as shown in FIG. 7F, the release liner 404 may not need to include any such corners 423. While the larger second portion 422 is shown by way of example only in FIG. 7F, the system 200 and the method 300 can also be used to provide the adhesive patch assembly 100 of FIGS. 1-5, in which the edges of the first portion 120 and the second portion 122 of the release liner 104 predominantly overlap, except for the reduced-radius corner 123. In such embodiments, the die shape of the second liner die 212 can be altered to form the desired shape of the second portion 122 of the release liner 104.

In the method 300 described above and illustrated in FIGS. 6 and 7A-7F, the patches 402 are positioned on the release liner 404 before the first portion 420 and the second portion 422 are provided or formed in the release liner 404 (i.e., island placement occurs before the release liner 404 is shaped). However, it should be understood that this need not be the case. Rather, in some embodiments, the release liner 404 can be formed or shaped (e.g., cut) to include the first portion 420 and at least part of the second portion 422, and then the patch 402 can be positioned on the release liner 404, such that the patch 402 is located on the second portion 422 of the release liner 404, while the first portion 420 of the release liner 404 is free of the patch 402.

The adhesive patch assemblies 100 and 400 are shown in the figures as separate embodiments for clarity in illustrating a variety of features of the adhesive patch assemblies of the present disclosure. However, it should be understood that any combination of elements and features of any of the embodiments illustrated in the figures and described herein can be employed in the adhesive patch assemblies of the present disclosure.

The following embodiments are intended to be illustrative of the present disclosure and not limiting.

Embodiments

Embodiment 1 is an adhesive patch assembly, the assembly comprising:
a patch including
a backing having a first major surface and a second major surface opposite the first major surface, and
a skin-contact adhesive coupled to the second major surface of the backing; and a release liner including
a first major surface and a second major surface opposite the first major surface, at least the first major surface configured to present release characteristics relative to the skin-contact adhesive of the patch,
a first portion and a second portion separated by a hinge, the first portion positioned to overlay the first major surface of the backing of the patch when the release liner is folded upon the hinge, and the second portion positioned to underlie at least one of the second major surface of the backing and the skin-contact adhesive of the patch;
wherein the first major surface of the release liner is positioned to face the patch when the patch is located between the first portion and the second portion of the release liner.

Embodiment 2 is a method of making an adhesive patch assembly, the method comprising:
providing a patch including a backing and a skin-contact adhesive coupled to the backing;
providing a release liner having a first portion and a second portion, wherein each of the first portion and the second portion are dimensioned to accommodate the patch;
positioning the patch on the release liner, such that patch is located on the second portion of the release liner and the first portion of the release liner is free of the patch; and
folding the release liner about a hinge located between the first portion and the second portion to locate the patch between the first portion and the second portion of the release liner.

Embodiment 3 is the assembly of embodiment 1 or the method of embodiment 2, wherein the coefficient of adhesion between the first major surface of the release liner and the first major surface of the backing of the patch is less than the coefficient of adhesion between the first major surface of the release liner and the skin-contact adhesive of the patch.

Embodiment 4 is an adhesive patch assembly, the assembly comprising:
a patch including
a backing having a first major surface and a second major surface opposite the first major surface, and
a skin-contact adhesive coupled to the second major surface of the backing; and a release liner including
a first major surface and a second major surface opposite the first major surface, at least the first major surface configured to present release characteristics relative to the skin-contact adhesive of the patch,
a first portion and a second portion separated by a hinge, the first portion positioned to overlay the first major surface of the backing of the patch when the release liner is folded upon the hinge, and the second portion positioned to underlie at least one of the second major surface of the backing and the skin-contact adhesive of the patch;

wherein the first major surface of the release liner is positioned to face the patch when the patch is located between the first portion and the second portion of the release liner, and wherein the coefficient of adhesion between the first major surface of the release liner and the backing of the patch is less than the coefficient of adhesion between the first major surface of the release liner and the skin-contact adhesive of the patch.

Embodiment 5 is the assembly of any of embodiments 1 and 3-4 or the method of embodiment 2, wherein, when the patch is located between the first portion and the second portion of the release liner, the release liner extends on all sides beyond a periphery of the patch.

Embodiment 6 is the assembly of any of embodiments 1 and 3-5 or the method of embodiment 2 or 5, wherein the release liner is sized such that the first portion and the second portion extend beyond all edges of the patch when the patch is located between the first portion and the second portion of the release liner.

Embodiment 7 is the assembly of any of embodiments 1 and 3-6 or the method of any of embodiments 2 and 5-6, wherein the first portion and the second portion of the release liner are integrally formed together.

Embodiment 8 is the assembly of any of embodiments 1 and 3-7 or the method of any of embodiments 2 and 5-7, wherein the hinge includes an integral hinge.

Embodiment 9 is the assembly of any of embodiments 1 and 3-8 or the method of any of embodiments 2 and 5-8, wherein the hinge is formed from at least one uncut point that connects the first portion and the second portion of the release liner.

Embodiment 10 is the assembly of any of embodiments 1 and 3-9 or the method of any of embodiments 2 and 5-9, wherein the release liner is formed from one sheet of material.

Embodiment 11 is the assembly of any of embodiments 1 and 3-10 or the method of any of embodiments 2 and 5-10, wherein the release liner comprises a monolithic construction.

Embodiment 12 is the assembly of any of embodiments 1 and 3-11 or the method of any of embodiments 2 and 5-11, wherein the release liner comprises a non-laminate construction.

Embodiment 13 is the assembly of any of embodiments 1 and 3-12 or the method of any of embodiments 2 and 5-12, wherein the release liner provides no adhesion to the backing of the patch.

Embodiment 14 is the assembly of any of embodiments 1 and 3-13 or the method of any of embodiments 2 and 5-13, wherein the patch assembly includes no additional layers located between the first major surface of the release liner and the patch.

Embodiment 15 is the assembly of any of embodiments 1 and 3-14 or the method of any of embodiments 2 and 5-14, wherein the patch assembly includes no additional layers located between the first major surface of the release liner and the backing of the patch.

Embodiment 16 is the assembly of any of embodiments 1 and 3-15 or the method of any of embodiments 2 and 5-15, wherein the patch assembly includes no additional layers located between the first major surface of the release liner and the skin-contact adhesive of the patch.

Embodiment 17 is the assembly of any of embodiments 1 and 3-16 or the method of any of embodiments 2 and 5-16, wherein the release characteristics of the first major surface are coextensive with the first major surface Embodiment 18 is the assembly of any of embodiments 1 and 3-17 or the method of any of embodiments 2 and 5-17, wherein the second portion of the release liner includes at least one of a slit and a tab.

Embodiment 19 is the assembly of any of embodiments 1 and 3-18 or the method of any of embodiments 2 and 5-18, wherein the second portion of the release liner forms a primary liner for the patch, and wherein the first portion of the release liner forms a cover liner.

Embodiment 20 is the assembly of any of embodiments 1 and 3-19 or the method of any of embodiments 2 and 5-19, wherein the release liner includes a first dimension that is at least twice a first dimension of the patch.

Embodiment 21 is the assembly of any of embodiments 1 and 3-20 or the method of any of embodiments 2 and 5-20, wherein the release liner includes a second dimension that is greater than a second dimension of the patch.

Embodiment 22 is the assembly of any of embodiments 1 and 3-21 or the method of any of embodiments 2 and 5-21, wherein the coefficient of adhesion between the first major surface of the release liner and the skin-contact adhesive of the patch is less than the coefficient of adhesion between the skin-contact adhesive and skin.

Embodiment 23 is the assembly of any of embodiments 1 and 3-22 or the method of any of embodiments 2 and 5-22, wherein the patch comprises a drug.

Embodiment 24 is the assembly of any of embodiments 1 and 3-23 or the method of any of embodiments 2 and 5-23, wherein the patch comprises a drug reservoir layer between the backing and the skin-contact adhesive.

Embodiment 25 is the assembly of any of embodiments 1 and 3-24 or the method of any of embodiments 2 and 5-24, wherein the patch comprises a skin penetration enhancer.

Embodiment 26 is the assembly of any of embodiments 1 and 3-25 or the method of any of embodiments 2 and 5-25, wherein the drug is selected from the group consisting of buprenorphine, clonidine, diclofenac, estradiol, granisetron, isosorbide dinitrate, levonorgestrel, lidocaine, methylphenidate, nicotine, nitroglycerine, oxybutynin, rivastigmine, rotigotine, scopolamine, selegiline, tulobuterol, fentanyl, and combinations thereof.

Embodiment 27 is the assembly of any of embodiments 1 and 3-26 or the method of any of embodiments 2 and 5-26, wherein the patch includes a transdermal drug delivery patch.

Embodiment 28 an article comprising the adhesive patch assembly of any of embodiments 1 and 3-27, wherein the adhesive patch assembly is packaged in a hermetically-sealed pouch.

Embodiment 29 is the method of any of embodiments 2 and 5-27, wherein providing a release liner having a first portion and a second portion occurs after the patch is positioned on the release liner, such that the release liner is provided, the patch is positioned on the release liner, and the first portion and second portion of the release liner are provided such that the patch is positioned on the second portion of the release liner but not the first portion of the release liner.

Embodiment 30 is the method of any of embodiments 2 and 5-29, further comprising forming at least a portion of the first portion and at least a portion the second portion in the release liner such that the first portion and the second portion of the release liner remain attached by at least one uncut point.

Embodiment 31 is the method of embodiment 30, wherein folding the release liner includes folding the release liner along a line that includes the at least one uncut point.

Embodiment 32 is the method of any of embodiments 2 and 5-31, wherein folding the release liner between the first portion and the second portion includes folding the first portion of the release liner over the patch and the second portion of the release liner.

Embodiment 33 is the method of any of embodiments 2 and 5-32, wherein the release liner is provided in roll form and is fed through a series of rolls that define a machine direction, and wherein the first portion of the release liner leads in the machine direction.

Embodiment 34 is the method of any of embodiments 2 and 5-33, wherein folding the release liner includes using a compressed air nozzle.

Embodiment 35 is the method of any of embodiments 2 and 5-34, wherein folding the release liner includes using a cross-web folding rod.

Embodiment 36 is the method of any of embodiments 2 and 5-35, wherein each of the first portion and the second portion of the release liner includes a first major surface and a second major surface opposite the first major surface, wherein the first major surface is positioned to face the patch when the patch is positioned on the release liner, and wherein at least the first major surface is configured to present release characteristics relative to the skin-contact adhesive of the patch.

Embodiment 37 is the method of any of embodiments 2 and 5-36, wherein:
the backing of the patch includes a first major surface and a second major surface,
the skin-contact adhesive of the patch is coupled to the second major surface of the backing,
the skin-contact adhesive of the patch is adhered to the second portion of the release liner when the patch is positioned on the release liner, and
the first portion of the release liner is positioned over the first major surface of the backing when the release liner is folded.

The following examples are intended to be illustrative of the present disclosure and not limiting.

EXAMPLES

Example 1

A Loparex 4400X release liner was supplied and die-cut with appropriate slits in a continuous motion. Adhesive patches were die-cut from 3M Blenderm 1525L Medical Tape to be approximately 0.75" (19.1 mm) in length and 0.7" (17.8 mm) in width. The die-cut patches were island-placed over the slits and the liner shapes were die-cut to about 1.1" (27.9 mm) in width and about 3" (76.2 mm) in length. The release liners were folded with a compressed air nozzle, and the completed adhesive patch assembly was about 1.5" (38.1 mm) in length. This 0.005" (0.13 mm) thick release liner resisted folding, so a 0.003" (0.08 mm) thick 3M ScotchPak 9744 release liner was used. Folding was improved, but with a small patch size such as this, the ~0.015" (0.38 mm)-wide uncut points should be reduced, to about 0.010" (0.25 mm) Static electricity was also observed to play a role in keeping the assembly folded. Static elimination bars appropriately placed over the webs improved folding stability.

Example 2

The same release liner material as that used in Example 1 was supplied and die-cut with appropriate slits in a continuous motion. Adhesive patches were die-cut from the same material as in Example 1 to be approximately 3.1" (78.7 mm) in length and 2.6" (66 mm) in width. The die-cut patches were island-placed over the slits and the liner shapes were die-cut to about 3" (76.2 mm) in width and about 7" (177.8 mm) in length. The release liners were folded with a compressed air nozzle, and the completed adhesive patch assembly was about 3.5" (88.9 mm) in length. The liners stayed folded in this size with both 0.003" (0.08 mm)- and 0.005" (0.13 mm)-thick release liners supplied.

Example 3

A 0.003" (0.08 mm) thick Scotchpak 9744 release liner was supplied and die-cut with appropriate slits in a continuous motion. Adhesive patches were die-cut from 3M Blenderm 1525L Medical Tape to be approximately 2.3" (58.4 mm) in length and 1.7" (43.2 mm) in width. The die cut patches were island-placed over the slits and the liner shapes were die-cut to be about 2.1" (53.3 mm) in width and about 5.8" (147.3 mm) in length. The release liners were folded with a compressed air nozzle, and the completed adhesive patch assembly was about 2.9" (73.7 mm) in length. The liners stayed folded in this size. Only the 0.003" (0.08 mm)-thick ScotchPak 9744 release liner was used in this trial.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

Various features and aspects of the present disclosure are set forth in the following claims.

What is claimed is:

1. An article comprising an adhesive patch assembly, the article comprising:
a patch having a periphery, the patch including:
a backing having a first major surface and a second major surface opposite the first major surface,
a skin-contact adhesive coupled to the second major surface of the backing,
a skin penetration enhancer,
a drug; and
a release liner including:
a first major surface and a second major surface opposite the first major surface, at least the first major surface configured to present release characteristics relative to the skin-contact adhesive of the patch,
a first portion and a second portion separated by a hinge, the first portion positioned to overlay the first major surface of the backing of the patch when the release liner is folded upon the hinge, and the second portion positioned to underlie at least one of the second major surface of the backing and the skin-contact adhesive of the patch;
wherein the first major surface of the release liner is positioned to face the patch when the patch is located between the first portion and the second portion of the release liner, and wherein the release characteristics of the first major surface of the first portion of the release liner are coextensive with the first major surface of the second portion of the release liner, wherein the first and second portions having said release characteristics extend a distance beyond the periphery of the patch when the patch is located between the first portion and the second portion of the release liner, and wherein the second portion includes a slit, and wherein the second portion further comprises two separate sections separated by the slit;

wherein the adhesive patch assembly is packaged in a separate and distinct hermetically-sealed pouch.

2. The assembly of claim 1, wherein a coefficient of adhesion between the first major surface of the release liner and the first major surface of the backing of the patch is less than a coefficient of adhesion between the first major surface of the release liner and the skin-contact adhesive of the patch.

3. The article of claim 1, wherein the release liner is formed from one sheet of material.

4. The article of claim 1, wherein the release liner comprises a monolithic construction.

5. The article of claim 1, wherein the release liner comprises a non-laminate construction.

6. The article of claim 1, wherein the release liner provides no adhesion to the backing of the patch.

7. The article of claim 1, wherein the patch assembly includes no additional layers located between the first major surface of the release liner and the patch.

8. The article of claim 1, wherein the second portion of the release liner includes a tab.

9. The article of claim 1, wherein the release liner includes a first dimension that is at least twice a first dimension of the patch, and wherein the release liner includes a second dimension that is greater than a second dimension of the patch.

10. The article of claim 1, wherein the drug is selected from the group consisting of buprenorphine, clonidine, diclofenac, estradiol, granisetron, isosorbide dinitrate, levonorgestrel, lidocaine, methylphenidate, nicotine, nitroglycerine, oxybutynin, rivastigmine, rotigotine, scopolamine, selegiline, tulobuterol, fentanyl, and combinations thereof.

11. The article of claim 1, wherein the first major surface of the second portion of the release liner is in contact with the first major surface of the backing of the patch when the patch is located between the first portion and the second portion of the release liner.

12. The article of claim 1, wherein the first and second portions of the release liner having coextensive release characteristics extend beyond the periphery of the patch by at least about ⅛ inch.

13. The article of claim 1, wherein the first and second portions of the release liner having coextensive release characteristics extend beyond the periphery of the patch by at least about ¼ inch.

14. The article of claim 1, wherein the release characteristics extends across the entire first major surface of the release liner.

15. A method of making an article comprising an adhesive patch assembly, the method comprising the steps of:

providing a patch having a periphery, the patch including a backing, a skin-contact adhesive coupled to the backing, a drug, and a skin penetration enhancer;

providing a release liner including a first major surface and a second major surface opposite the first major surface, at least the first major surface configured to present release characteristics relative to the skin-contact adhesive of the patch, the release liner having a first portion and a second portion, wherein each of the first portion and the second portion are dimensioned to accommodate the patch, and wherein the release characteristics of the first major surface of the first portion of the release liner are coextensive with the first major surface of the second portion of the release liner;

including a slit into the second portion of the release liner, wherein the second portion further comprises two separate sections separated by the slit;

positioning the patch on the release liner, such that patch is located on the second portion of the release liner and the first portion of the release liner is free of the patch, wherein when the patch is located between the first portion and the second portion of the release liner the first and second portions having said release characteristics extend a distance beyond the periphery of the patch;

folding the release liner about a hinge located between the first portion and the second portion to locate the patch between the first portion and the second portion of the release liner and to form an adhesive patch assembly; and packaging the adhesive patch assembly in a separate and distinct hermetically-sealed pouch.

16. The method of claim 15, wherein providing a release liner having a first portion and a second portion occurs after the patch is positioned on the release liner, such that the release liner is provided, the patch is positioned on the release liner, and the first portion and second portion of the release liner are provided such that the patch is positioned on the second portion of the release liner but not the first portion of the release liner.

17. The method of claim 15, further comprising forming at least a portion of the first portion and at least a portion the second portion in the release liner such that the first portion and the second portion of the release liner remain attached by at least one uncut point.

18. The method of claim 17, further comprising removing the adhesive patch assembly from a continuous web after folding the release liner about the hinge.

19. The method of claim 15, wherein the release liner is provided in roll form and is fed through a series of rolls that define a machine direction, and wherein the first portion of the release liner leads in the machine direction.

20. The method of claim 15, wherein folding the release liner includes using a compressed air nozzle.

21. The method of claim 15, wherein folding the release liner includes using a cross-web folding rod.

* * * * *